United States Patent
Mereu et al.

(10) Patent No.: US 9,163,025 B2
(45) Date of Patent: Oct. 20, 2015

(54) STABLE COMPLEXES OF AN ALKALINE EARTH METAL SALT OF $N^5$-METHYL-TETRAHYDROFOLIC ACID AND A POLYOL

(71) Applicant: CERBIOS-PHARMA SA, Barbengo/Lugano (CH)

(72) Inventors: Andrea Mereu, Barbengo/Lugano (CH); Maurizio Massara, Barbengo/Lugano (CH); Alessandro Vadala', Barbengo/Lugano (CH)

(73) Assignee: CERBIOS-PHARMA SA, Barbengo (Lugano) (CH)

( * ) Notice: Subject to any disclaimer, the term of this patent is extended or adjusted under 35 U.S.C. 154(b) by 0 days.

(21) Appl. No.: 14/516,035

(22) Filed: Oct. 16, 2014

(65) Prior Publication Data

US 2015/0152110 A1 Jun. 4, 2015

(30) Foreign Application Priority Data

Dec. 2, 2013 (EP) ..................................... 13195344

(51) Int. Cl.
*C07D 475/04* (2006.01)
*A61K 31/519* (2006.01)

(52) U.S. Cl.
CPC ............ *C07D 475/04* (2013.01); *A61K 31/519* (2013.01)

(58) Field of Classification Search
CPC ..................................................... C07D 475/04
See application file for complete search history.

(56) References Cited

FOREIGN PATENT DOCUMENTS

EP 1695975 8/2006

OTHER PUBLICATIONS

Hamalainen, M. M., et al., Polyol-Mineral Interactions in the Diet of the Rat . . . , Nutrition Research, vol. 9, No. 7, pp. 801-811, 1989.
European Search Report corresponding to EP priority application 13195344.0, (2014).

*Primary Examiner* — Bruck Kifle
(74) *Attorney, Agent, or Firm* — Lucas & Mercanti, LLP

(57) ABSTRACT

Complexes between an alkaline earth metal salt of (6RS)— or (6S)—$N^5$-methyl-(5,6,7,8)-tetrahydrofolic acid and a polyol were prepared by lyophilization or spray-drying. These products were found to be stable compared with the active ingredient alone or the mixture of the same components prepared by means of other methodologies.

9 Claims, No Drawings

STABLE COMPLEXES OF AN ALKALINE EARTH METAL SALT OF $N^5$-METHYL-TETRAHYDROFOLIC ACID AND A POLYOL

CROSS-REFERENCE TO RELATED APPLICATIONS

This application claims priority of European Patent Application No. 13195344.0, filed Dec. 2, 2013, the contents of which are incorporated herein by reference.

The present invention relates to stable complexes between an alkaline earth metal salt of (6RS)— or (6S)—$N^5$-methyl-tetrahydrofolic acid and a polyol and to their use for the preparation of pharmaceutical or nutraceutical formulations.

BACKGROUND OF THE INVENTION

Folic acid and the corresponding (5,6,7,8)-tetrahydrofolates are very important in several therapeutic areas. Folic acid facilitates protection against the risk of several congenital malformations, including neural tube defects, such as spina bifida, anencephaly and encephalocele.

One of the therapeutically widely used tetrahydrofolate is (6S)—$N^5$-methyl-(5,6,7,8)-tetrahydrofolic acid calcium salt (1) ($C_{20}H_{25}N_7O_6 \cdot Ca$; CAS Registry Number: 151533-22-1).

(1)

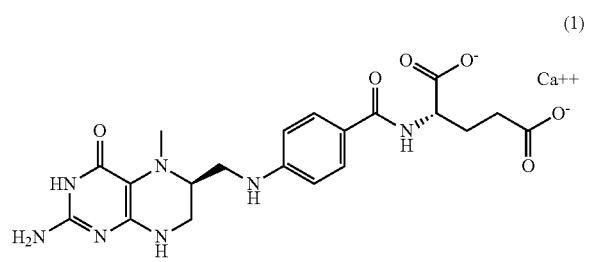 [SMILES: CN1c2c(nc(N)[nH]c2=O)NC[C@@H]1CNc1ccc(C(=O)N[C@@H](CCC(=O)[O-])C(=O)[O-])cc1 ; [Ca+2]]

$N^5$-Methyl-tetrahydrofolic acid and salts thereof are therapeutically relevant for the treatment of megaloblastic anaemia, as antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic formulations, for instance trimethoprim-sulfamethoxazole, and for reducing the toxicity of dideazatetrahydrofolates in chemotherapy.

$N^5$-Methyl-tetrahydrofolate alkaline earth metal salts are used in particular as food additive or as a vitamin preparation, for the prevention of neural tube defects, for the treatment of depressive illnesses, and for decreasing the homocysteine level.

$N^5$-Methyl-tetrahydrofolic acid and salts thereof are extremely unstable, and in particular are highly susceptible to oxidation [see for instance A. L. Fitzhugh, Pteridines 4 (4), 187-191 (1993)].

It is therefore difficult to produce them at a level of purity which is acceptable for a pharmaceutical active ingredient or a food additive.

Typical degradation pathways of $N^5$-methyltetrahydrofolate, leading to the characteristic impurities 4α-hydroxy-5-methyltetrahydrofolic acid (D1) and pyrazino-s-triazine derivative (D2a and D2b), are outlined in Schemes 1 and 2.

Scheme 1: 4α-hydroxy-5-methyltetrahydrofolic acid (D1)

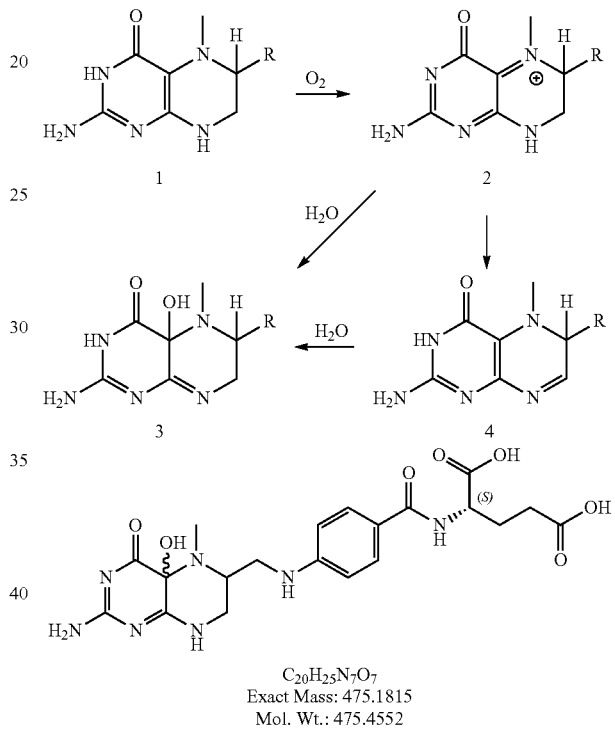

$C_{20}H_{25}N_7O_7$
Exact Mass: 475.1815
Mol. Wt.: 475.4552

Scheme 2: pyrazino-s-triazine derivative (D2)

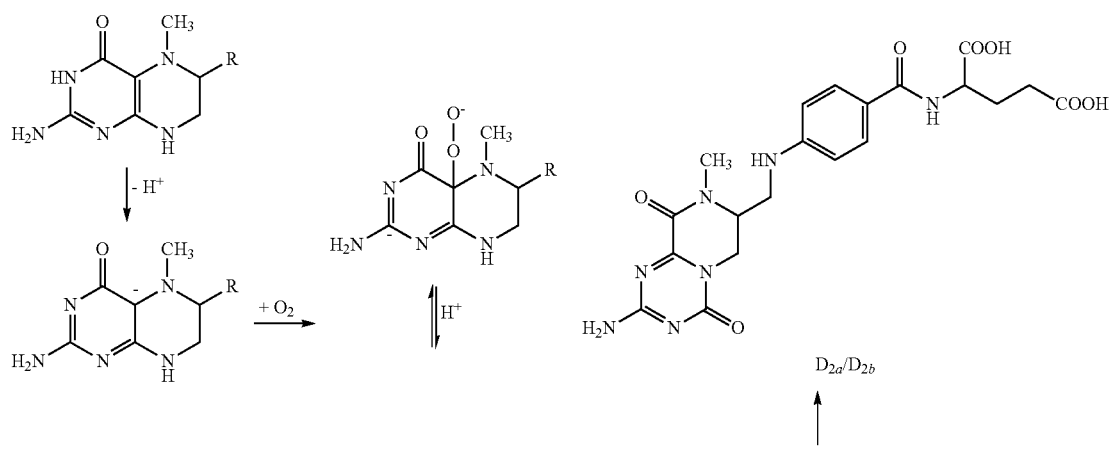

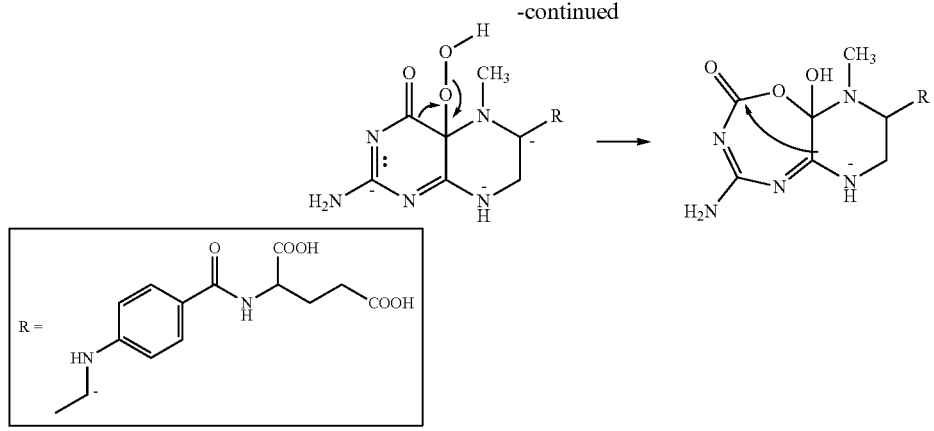

Various methods, such as excluding oxygen as completely as possible or the addition of antioxidants such as ascorbic acid or reduced L-glutathione, have been employed in order to overcome the instability of 5-methyl-tetrahydrofolic acid.

However, it is scarcely possible to completely exclude oxygen during use, and even then this is only possible at very considerable cost, and the addition of antioxidants is likewise not always possible.

Therefore there is the need to find a method for the stabilization of (6S)—$N^5$-methyl-tetrahydrofolate salts.

The use of stabilizing agents was described in the prior art.

For example WO 2011/018482 (Bayer Schering Pharma AG) discloses stabilised particles comprising a crystalline form of an alkaline earth metal salt of (6S)—$N^5$-methyl-tetrahydrofolic acid and at least one protective agent.

The preparation of formulations of $N^5$-methyl-tetrahydrofolate salts is considered problematic as it can result in the partial decomposition of the active ingredient as reported for example in WO 2008/003432 (Bayer Schering Pharma AG).

EP 1 044 975 (Eprova AG) discloses a preparation of stable crystalline forms of (6S)—$N^5$-methyltetrahydrofolic acid calcium salt by treatment of the product at high temperature, which is technically problematic for large scale production.

U.S. Pat. No. 7,947,662 (Gnosis SpA) discloses pharmaceutical compositions of folates derivatives stabilized as glucosamine salts.

U.S. Pat. No. 5,455,236 (Eprova AG) discloses the use of cyclodextrin to include and stabilize tetrahydrofolate derivatives.

The use of these additives in pharmaceutical formulations is not always desirable.

DESCRIPTION OF THE INVENTION

We have now found that the formation of a complex between $N^5$-methyl tetrahydrofolates salts and polyols leads to a stable product that can be safely used for the preparation of pharmaceutical and nutraceutical formulations.

Therefore, object of the present invention is a stable complex of an alkali earth metal salt of (6RS) or (6S)—$N^5$-methyl tetrahydrofolic acid with a polyol.

Preferably the alkali earth metal salt of (6RS)— or (6S)—$N^5$-methyl-(5,6,7,8)-tetrahydrofolic acid is calcium salt.

Suitable polyols include also cyclic polyols, particularly polyalcohols conventionally used in the pharmaceutical and nutraceutical field such as for example mannitol, sorbitol, isomaltol and inositol.

Mannitol is particularly preferred.

In the complexes object of the present invention the molar ratio between the polyol and the $N^5$-methyl-(5,6,7,8)-tetrahydrofolate salt is between 1 and 10.

The complexes object of the present invention can be obtained through a wide range of procedures. Among these procedures spray-drying and liophylization technologies are particularly preferred because they were found to be the more efficient and capable to yield a product characterized by high purity and stability.

For the spray-drying as well as for the liophylization process, a solution of the alkali earth metal salt of (6RS)— or (6S)—$N^5$-methyl-(5,6,7,8)-tetrahydrofolic acid and the polyol in a suitable solvent is prepared.

The preferred solvent is water, which can be optionally in admixture with other solvents, preferably lower alcohols, such methanol and ethanol.

When lyophilization is used for the preparation of the complexes object of the present invention, the preferred suitable solvent is an admixture of water with a lower alcohol.

The spray-drying and lyophilization processes for the preparation of the complexes object of the present invention are carried out according to conventional procedures.

Preferably the spray-drying process is carried out using an inlet temperature between 120° C. and 150° C., an outlet temperature between 50° C. and 80° C. and a process pressure between 20 mmHg and 50 mmHg.

The possibility of using spray-drying and lyophilization procedures for the preparation of the complexes of the present invention offers several additional advantages over other procedures, such as better process control and easy scale up.

The complexes of an alkaline earth metal salt of $N^5$-methyl-(5,6,7,8)-tetrahydrofolic acid with a polyol according to the present invention are more stable than the corresponding $N^5$-methyl-(5,6,7,8)-tetrahydrofolic acid salt alone.

This stability makes them particularly suitable for the preparation of pharmaceutical or nutraceutical formulations.

The present invention is now illustrated by the following examples without limiting it.

EXAMPLES

Example 1

Preparation of (6S)—$N^5$-methyl-(5,6,7,8)-tetrahydrofolate calcium salt according to the procedure described in CH699426

106.9 g of (6S)—$N^5$-methyl-tetrahydrofolic acid were dissolved in 400 ml of water at 40° C. by addition of aqueous NaOH solution to obtain pH of 6.8.

0.90 equivalents of $CaCl_2$ were added to this solution and the precipitation of the calcium salt of (6S)—$N^5$-methyl-(5,6,7,8)-tetrahydrofolic acid started by seeding with 100 mg product. The mixture was stirred 1 hour at 40° C., cooled at 23° C. in 2 hours and this temperature was maintained for 18 hours. The suspension was filtered and the solid washed with water and ethanol. After being dried under reduced pressure, 47.3 g of (6S)—$N^5$-methyl-(5,6,7,8)-tetrahydrofolate calcium salt (5MeTHF) were obtained.

Example 2

Evaporation Experiment at Room Temperature

Calcium (6S)—$N^5$-methyl-(5,6,7,8)-tetrahydrofolate (3 g) and mannitol (6 g) were dissolved into 300 mL of water and stirred at room temperature. The solution was left to evaporate at room temperature and reduced pressure to yield reference compound EVRT.

The compound EVRT was subjected to accelerated stability studies. Its stability data are reported in Table 2.

Example 3

Evaporation Experiment at 4° C.

Calcium (6S)—$N^5$-methyl-(5,6,7,8)-tetrahydrofolate (3 g) and mannitol (6 g) were dissolved into 300 mL of water and stirred at room temperature. The solution was left to evaporate at 4° C. and reduced pressure to yield reference compound EVLT.

The compound EVLT was subjected to accelerated stability studies. Its stability data are reported in Table 2.

Example 4

Evaporation Experiment at 60° C.

Calcium (6S)—$N^5$-methyl-(5,6,7,8)-tetrahydrofolate (3 g) and mannitol (6 g) were dissolved into 300 mL of water and stirred at room temperature. The solution was left to evaporate at 60° C. at reduced pressure to yield reference compound EVHT.

The compound EVHT was subjected to accelerated stability studies. Its stability data are reported in Table 2.

Example 5

Spray-Drying Experiments

Calcium (6S)—$N^5$-methyl-(5,6,7,8)-tetrahydrofolate (5 g) and mannitol (10 g, 5eq.) were dissolved and stirred at room temperature into a volume from 300 to 1000 mL of water or a mixture of water and methanol (MET) or ethanol (ETH). The solution was spray-dried by means of a Mini Spray Dryer B-290 (Buchi) and the complex recovered. Significant experimental conditions and instrumental settings are reported in Table 1.

Some of the obtained products, namely SD-3, SD-4, SD-6, SD-7, SD-8, SD-9, SD10 (the code number corresponds to the experiment number), were subjected to accelerated stability studies. Their stability data are reported in Table 2.

Example 6

Spray-Drying Experiments

Calcium (6S)—$N^5$-methyl-(5,6,7,8)-tetrahydrofolate (5 g) and inositol (10 g) were dissolved and stirred at room temperature into a volume of 500 mL water. The solution was spray-dried by means of a Mini Spray Dryer B-290 (Buchi) and the complex recovered.

Example 7

Lyophilization Experiments

Calcium (6S)—$N^5$-methyl-(5,6,7,8)-tetrahydrofolate (3 g) and mannitol (API/mannitol ratio varied from 1/10 to 1/1) were mixed in water (300 mL) and stirred at room temperature until a clear yellow solution was obtained. Time of stirring was found to vary from 10 to 30 minutes depending on products and water ratio. The pH values of the obtained solutions varied in the range between 6.7 to 7.3. The solutions were placed in amber glass flasks in re-freeze drying equipment (Edward Minifast 2000 SN:3028). The product was frozen for 1 day, vacuum applied, the system brought to 0° C. and maintained at 0° C. for 1 day. The system temperature was increased by 5° C. about every six hours until 20° C. were reached.

The products were recovered. The products from Lyo-1 and Lyo-6 were subjected to stabilities studies which results are reported in Table 2.

Example 8

Determination of related substances of calcium (6S)—$N^5$-methyl-(5,6,7,8)-tetrahydrofolate by HPLC method Sample Preparation:

25±3 mg of (6S)-5-methyl-tetrahydrofolic acid calcium salt calculated on dry base were placed in a 50 ml volumetric flask and added with 320 µl of acid ascorbic solution and water until the final volume was reached. The solution was transferred in a HPLC vial and the sample injected immediately.

Analysis: 10 µl of the sample solution were Injected, the chromatogram recorded (analytical wavelength 280±16 nm) and the peak response measured.

Chromatographic System:

the liquid chromatograph was equipped with a Hypersil ODS column (length 250 mm, ID 4 mm, particle size 5 µm).

TABLE 1

Spray-drying experiments

| | 5MeTHF (g) | Mannitol (g) | Solvent | Volume (L) | 5MeTHF (g/L) | Gas | Inlet Temp. [° C.] | Out Temp. [° C.] | Pump rate | Aspiration | Gas Pressure |
|---|---|---|---|---|---|---|---|---|---|---|---|
| Exp 1 | 5.0 | 10.0 | $H_2O$ | 0.5 | 10.0 | $N_2$ | 140 | 67 | 30 | 100 | 40 |
| Exp 2 | 5.0 | 10.0 | $H_2O$ | 0.5 | 10.0 | $N_2$ | 140 | 52 | 30 | 100 | 40 |
| Exp 3 | 5.0 | 10.0 | $H_2O$ | 0.5 | 10.0 | $N_2$ | 140 | 77 | 30 | 100 | 40 |
| Exp 4 | 4.7 | 9.4 | $H_2O$ | 1 | 4.7 | $N_2$ | 140 | 66 | 30 | 100 | 40 |
| Exp 5 | 4.9 | 10.0 | $H_2O$/MET 6/1 | 0.7 | 7.0 | Air | 140 | 59 | 40 | 100 | 40 |
| Exp 6 | 4.9 | 9.9 | $H_2O$/ETH 6/1 | 0.6 | 8.2 | Air | 130 | 60 | 30 | 100 | 40 |
| Exp 7 | 4.8 | 9.6 | $H_2O$ | 0.5 | 9.6 | Air | 140 | 59 | 30 | 100 | 40 |
| EXP 8 | 5.0 | 10.0 | $H_2O$ | 0.5 | 9.9 | Air | 140 | 64 | 20 | 100 | 40 |
| Exp 9 | 4.8 | 9.8 | $H_2O$ | 0.35 | 13.8 | Air | 140 | 66 | 20 | 100 | 40 |
| Exp 10 | 5.0 | 10.1 | $H_2O$ | 0.35 | 14.4 | Air | 140 | 67 | 20 | 100 | 30 |

The column was coupled with a diode array detector for the detection wavelength of 280±16 nm
Mobile Phase:
Solution A: 0.05 M $NaH_2PO_4$, pH 6.50,
Solution B: 0.03 M $NaH_2PO_4$ in water/methanol 65/35, pH 8.0
Gradient: from 100% A to 100% B
Flow rate: 1.1 ml/min; column temperature: 30° C.; run time: 22 min.

Example 9

Determination of assay by HPLC of calcium (6RS) and (6S) $N^5$-methyl-tetrahydrofolate Sample Preparation:
75-85 mg of sample were dissolved in 200 ml water within a 250 ml volumetric flask. 1 ml of the ascorbic acid solution was added and dilute to 250 ml with water. A total of three sample solutions were prepared.
Analysis:
The HPLC system was verified and calibrated by injecting the standard solutions. Once each of the three prepared sample solutions were injected followed by one standard solution as calibration control.
Chromatographic System:
The liquid chromatograph was equipped with an analytical column such ACE 5 $C_{18}$, 250 mm×2.1 mm, with particle size 5 µm.
Mobile Phase Composition:
acetonitrile 12%, phosphate buffer pH 6.5 80%, methanol+ 2-mercaptoethanol 8%.
Other Chromatographic Parameters:
column temperature: 25° C., isocratic mode, flow rate: 0.41 ml/min, injection volume: 5 µl, run time: 13.5 min, analytical wavelength: 290 nm.

Example 10

Stability Tests

The stability of the complexes according to the present invention prepared by spray-drying or lyophilization as described in examples 5 and 7 was tested in comparison with the stability of (6S)—$N^5$-methyl-tetrahydrofolate calcium salt alone. Preparations obtained through different technologies, such as evaporation of the solvent from the solution, as reported in examples 2, 3 and 4, were also assessed for stability. Accelarated stability experiments at 25° C. and 40% relative humidity were carried out.
The obtained stability data are reported in the following Table 2.

TABLE 2

Accelerated stability of calcium (6S) N5-methyl-tetrahydrofolate products

| Product | Increase of D2 % content | | | Decrease of 5MeTHF % content | | |
|---|---|---|---|---|---|---|
|  | 4 weeks | 12 weeks | 24 weeks | 4 weeks | 12 weeks | 24 weeks |
| 5MeTHF | 1.30 | 1.40 | 2.3 | −2.70 | −2.80 | −5.6 |
| EVLT | 0.75 | 1.87 | 3.12 | −1.98 | −3.66 | −6.25 |
| EVRT | 0.75 | 1.49 | 2.38 | −1.34 | −2.04 | −3.56 |
| EVHT | 0.14 | 0.41 | 1.48 | −0.31 | −0.47 | −2.57 |
| SD-3 | 0.06 | 0.03 | 0.28 | −0.13 | −0.08 | −0.37 |
| SD-4 | 0.23 | 0.29 | 0.72 | −0.41 | −0.46 | −1.07 |
| SD-6 | 0.24 | 0.59 | 0.95 | −0.38 | −1.00 | −1.49 |
| SD-7 | 0.16 | 0.47 | 0.56 | −0.17 | −0.71 | −0.84 |
| SD-8 | 0.06 | 0.15 | 0.37 | −0.10 | −0.19 | −0.53 |
| SD-9 | 0.11 | 0.12 | 0.38 | −0.29 | −0.30 | −0.63 |
| SD-10 | 0.24 | 0.33 | 0.67 | −0.44 | −0.57 | −1.03 |
| Lyo-1 | 0.03 | 0.06 | 0.09 | −0.05 | −0.09 | −0.24 |
| Lyo-2 | 0.04 | 0.16 | 0.23 | 0.00 | −0.19 | −0.41 |
| Lyo-3 | 0.05 | 0.13 | 0.27 | 0.00 | −0.15 | −0.24 |
| Lyo-4 | 0.01 | 0.02 | 0.03 | 0.00 | −0.06 | −0.17 |
| Lyo-5 | 0.02 | 0.08 | 0.23 | −0.06 | 0.00 | −0.40 |
| Lyo-6 | 0.02 | 0.06 | 0.13 | −0.21 | 0.02 | −0.01 |

The results described in Table 2 demonstrate that the complexes between $N^5$-methyl-tetrahydrofolate and a polyol resulted to be much more stable than the active ingredient alone (5MeTHF) or the products obtained by simple evaporation of the solution of methyl-tetrahydrofolate and a polyol (EVLT, EVRT, EVHT). Preparations obtained by lyophilization (Lyo-1, Lyo-2, Lyo-3, Lyo-4, Lyo-5, Lyo-6) and spray-drying (SD-3, SD4, SD-6, SD-7, SD-8, SD-9, SD10) technologies gave the best results.

The invention claimed is:
1. A stable complex between an alkaline earth metal salt of (6RS)— or (6S)—$N^5$-methyl-(5,6,7,8)-tetrahydrofolic acid and a polyol.
2. The complex according to claim 1 wherein the polyol is selected among mannitol, sorbitol, isomaltol and inositol.
3. The complex according to claim 1 wherein the alkaline earth metal salt is the calcium salt.
4. The complex according to claim 1 wherein the molar ratio between the polyol and the $N^5$-methyl-(5,6,7,8)-tetrahydrofolate salt is between 1 and 10.
5. A process for the preparation of a stable complex between an alkaline earth metal salt of (6RS)— or (6S)—$N^5$-Methyl-(5,6,7,8)-tetrahydrofolic acid and a polyol, comprising lyophilizing a solution of the tetrahydrofolate salt and the polyol in a suitable solvent.
6. A process for the preparation of a stable complex between alkaline earth metal salt of (6RS)— or (6S)—$N^5$-Methyl-(5,6,7,8)-tetrahydrofolic acid and a polyol, comprising spray-drying of a solution of the tetrahydrofolate salt and the polyol in a suitable solvent.
7. The process according to claim 6 wherein the spray-drying is performed using an inlet temperature between 120° C. and 150° C., an outlet temperature between 50° C. and 80° C. and a process pressure between 20 mmHg and 50 mmHg.
8. The process according to claim 5 wherein the suitable solvent is water or a mixture of water with a lower alcohol.
9. The process according to claim 6 wherein the suitable solvent is water or a mixture of water with a lower alcohol.

* * * * *